United States Patent
Ungureanu et al.

(10) Patent No.: US 9,826,912 B2
(45) Date of Patent: Nov. 28, 2017

(54) PHOTOPLETHYSMOGRAPHIC DEVICE FOR MEASURING A HEART RHYTHM

(71) Applicant: LIVASSURED B.V., Vught (NL)

(72) Inventors: Constantin Ungureanu, Vught (NL); Theo Ary Asmund Tielens, Vught (NL)

(73) Assignee: LIVASSURED B.V., Vught (NL)

( * ) Notice: Subject to any disclaimer, the term of this patent is extended or adjusted under 35 U.S.C. 154(b) by 0 days.

(21) Appl. No.: 15/297,481

(22) Filed: Oct. 19, 2016

(65) Prior Publication Data
US 2017/0127958 A1    May 11, 2017

Related U.S. Application Data

(60) Provisional application No. 62/253,747, filed on Nov. 11, 2015.

(51) Int. Cl.
*A61B 5/024* (2006.01)
*A61B 5/00* (2006.01)

(52) U.S. Cl.
CPC ........ *A61B 5/02416* (2013.01); *A61B 5/0002* (2013.01); *A61B 5/02438* (2013.01);
(Continued)

(58) Field of Classification Search
None
See application file for complete search history.

(56) References Cited

U.S. PATENT DOCUMENTS 6,575,912 B1 *  6/2003  Turcott ............. A61B 5/02427
                                                    600/480
2002/0038081 A1  3/2002  Fein et al.
(Continued)

FOREIGN PATENT DOCUMENTS

| WO | 2014089665 A1 | 6/2014 |
| WO | 2015101947 A1 | 7/2015 |
| WO | 2015139980 A1 | 9/2015 |

OTHER PUBLICATIONS

Dresher, Russell, "Wearable Forehead Pulse Oximetry: Minimization of Motion and Pressure Artifacts", A Thesis Submitted to the Faculty of the Worcester Polytechnic Institute, May 3, 2006, pp. 1-93, Worcester Polytechnic Institute, Worcester, MA.

*Primary Examiner* — Brian T Gedeon
(74) *Attorney, Agent, or Firm* — Hudak, Shunk & Farine Co., LPA

(57) ABSTRACT

Photoplethysmographic device for measuring a heart rhythm, comprising a housing having a contacting surface and a control unit, a photoplethysmographic sensor mechanically attached to the contacting surface and connected to the control unit, wherein the control unit is arranged to receive a photoplethysmographic signal from the photoplethysmographic sensor, a fastening band having a first end and a second end, the first end and second end attached to the device for attaching the device to a subject with the contacting surface contacting the subject's skin, a pressure sensor attached to the contacting surface in close proximity to the photoplethysmographic sensor. The control unit is arranged determining whether the pressure from the pressure sensor is in a range suitable for photoplethysmographic measurement by the photoplethysmographic sensor.

11 Claims, 2 Drawing Sheets

(52) U.S. Cl.
CPC ............ *A61B 5/681* (2013.01); *A61B 5/6831* (2013.01); *A61B 5/6843* (2013.01); *A61B 5/746* (2013.01)

(56) References Cited

U.S. PATENT DOCUMENTS

| | | |
|---|---|---|
| 2007/0055163 A1 | 3/2007 | Asada et al. |
| 2009/0227965 A1 | 9/2009 | Wijesiriwardana |
| 2010/0168531 A1 | 7/2010 | Shaltis et al. |
| 2010/0241011 A1 | 9/2010 | McCombie et al. |
| 2013/0030259 A1 | 1/2013 | Thomsen et al. |
| 2013/0060098 A1 | 3/2013 | Thomsen et al. |
| 2013/0289889 A1 | 10/2013 | Yuen et al. |
| 2014/0107493 A1 | 4/2014 | Yuen et al. |
| 2014/0257058 A1 | 9/2014 | Clarysse et al. |
| 2015/0157720 A1 | 6/2015 | Fish et al. |
| 2015/0190077 A1 | 7/2015 | Kim et al. |
| 2015/0265214 A1 | 9/2015 | De Kok et al. |
| 2015/0265217 A1 | 9/2015 | Penders et al. |
| 2015/0286277 A1* | 10/2015 | Kim ........................ G06F 1/163 345/156 |

\* cited by examiner

PHOTOPLETHYSMOGRAPHIC DEVICE FOR MEASURING A HEART RHYTHM

FIELD OF THE INVENTION

The invention relates to a photoplethysmograpicy device for measuring a heart rhythm.

BACKGROUND OF THE INVENTION

Photoplethysmographic (PPG) measuring of heart rhythm uses a light source such as a Light Emitting Diode (LED) which irradiates light into a subject's skin. Light reflected from deeper layers in the skin is detected by a photodetector. Alternatively, light transmitted through the skin and tissue may be measured. As the blood flow through the skin varies with every heartbeat, so does the reflection or transmission of the light in or through the skin vary. The variation is detected by a control circuit and a heart rhythm may be determined from this variation.

PPG sensors can be integrated in wearables such as cuffs arranged for heart rhythm measurement, wristbands of smartwatches and the like.

The amplitude of a PPG signal from such PPG sensor in reflection and transmission mode depends on the pressure exerted by the sensor and the LED to the skin. Normally there is an optimal pressure wherein the amplitude of PPG signals is maximum. There is however for the wearer no easy way to know if the PPG signal has the highest amplitude when the sensor is attached on the skin. A wearer does not have a feedback on how tight they should wear the PPG sensor. Usually wearer instructions are vague and wearers tend to wear the sensor more tightly than is required. This may lead among other things to skin irritation. A wearer can use trial and error to find out which tightness works best. Alternatively a varying tightening force can be applied using an actuator until the desired signal strength is obtained.

Such strategies however can be time consuming and bulky, whereas a wearer may want a measurement on short notice. Moreover, comfortability decreases with contact pressure. When the fastening band is loose (e.g. as a wearer would normally wear a watch) there is a bad contact pressure and no PPG signal can be measured. If the fastening band or bracelet is too tight this will lead to pain because the skin is compressed. In addition, a too tight fastening band will have a detrimental effect on the PPG signal since the compressed capillaries will decrease the blood circulation. The optimum contact pressure is somewhere in the middle, not more than what is comfortable and enough for a good PPG signal.

SUMMARY OF THE INVENTION

It is an object of the invention to provide a device capable of measuring a heart rhythm immediately when sufficient pressure is exerted by the photoplethysmographic sensor to a subject's skin while preserving comfortability for a subject wearing the device.

The object is achieved in a photoplethysmographic device for measuring a heart rhythm, comprising a housing having a contacting surface and a control unit, a photoplethysmographic sensor mechanically attached to the contacting surface and connected to the control unit, wherein the control unit is arranged to receive a photoplethysmographic signal from the photoplethysmographic sensor, wherein the control unit is arranged for determining a heart rhythm from the photoplethysmographic signal. The device has a fastening band having a first end and a second end, the first end and second end attached to the device for attaching the device to a subject with the contacting surface contacting the subject's skin, and a pressure sensor attached to the contacting surface in close proximity to the photoplethysmographic sensor. The control unit is arranged for determining whether the pressure from the pressure sensor of is in a range suitable for photoplethysmographic measurement by the photoplethysmographic sensor.

The pressure sensor allows direct measurement of the pressure of the back of the housing with the photoplethysmographic sensor to the subject's skin. The determining whether the pressure from the pressure sensor of is in a range suitable for photoplethysmographic measurement by the photoplethysmographic sensor allows the device to be used efficiently and immediately without extensive evaluation of the photoplethysmographic signal.

In an embodiment the control unit is arranged for comparing a pressure signal strength with a first threshold value.

This allows determination whether the pressure is high enough.

In an embodiment the control circuit is further arranged for comparing the pressure signal strength with a second threshold value. The second threshold value being higher than the first threshold value.

This allows determination whether the pressure is not too high. The combination of both threshold values allows determination whether the pressure falls in a range limited by the first and second threshold value wherein photoplethysmographic measurement by the photoplethysmographic sensor is deemed reliable enough.

In an embodiment, the device further comprises an indicator connected to the control unit, wherein the control unit is arranged for activating the indicator when the pressure signal strength is equal to or exceeds the first threshold value and the pressure signal strength is equal to or less than the second threshold value.

This allows a user or wearer of the device to use the indication of the indicator to be made aware that the tightness of the fastening band is suitable for reliable photoplethysmographic measurement by the photoplethysmographic sensor.

In an embodiment the indicator is an audible alarm. This allows a user or wearer of the device to be aware of the correct tightness directly without having to visually check the device.

In an embodiment the control unit is arranged for determining a reliability factor for the PPG measurements from the pressure signal, and determining a heart rhythm using an actual photoplethysmographic measurement and a running history of measurements of the photoplethysmographic signal and wherein a measurement of the photoplethysmographic signal is saved in the running history when the reliability factor is higher than a threshold.

This allows for the determination of the heart rhythm when the reliability of the PPG signal is low, to rely more on historic PPG measurements and when the reliability of the PPG signal is high, to rely more on the actual PPG measurement. This way it can be compensated for movement artefacts in the PPG signal. When for example the photoplethysmographic device moves when the subject moves, causing artefacts in the photoplethysmographic signal, the heart rhythm indicated will be stable.

In an embodiment the photoplethysmographic sensor has a light source, and the control unit is arranged for comparing the pressure signal strength with a third threshold value. The control unit is further arranged for deactivating the light source in the photoplethysmographic sensor when the pressure signal strength is equal to or less than the third threshold value.

This prevents eye damage for a user when accidentally looking at the photoplethysmographic sensor light source, when the device is not properly attached to the subject's arm, wrist or limb.

In an embodiment, at least one of the photoplethysmographic sensor and the pressure sensor are mounted flush with the contacting surface. This contributes to the comfort of the subject's comfort wearing the photoplethysmographic device.

DETAILED DESCRIPTION OF THE INVENTION

Figure 1:
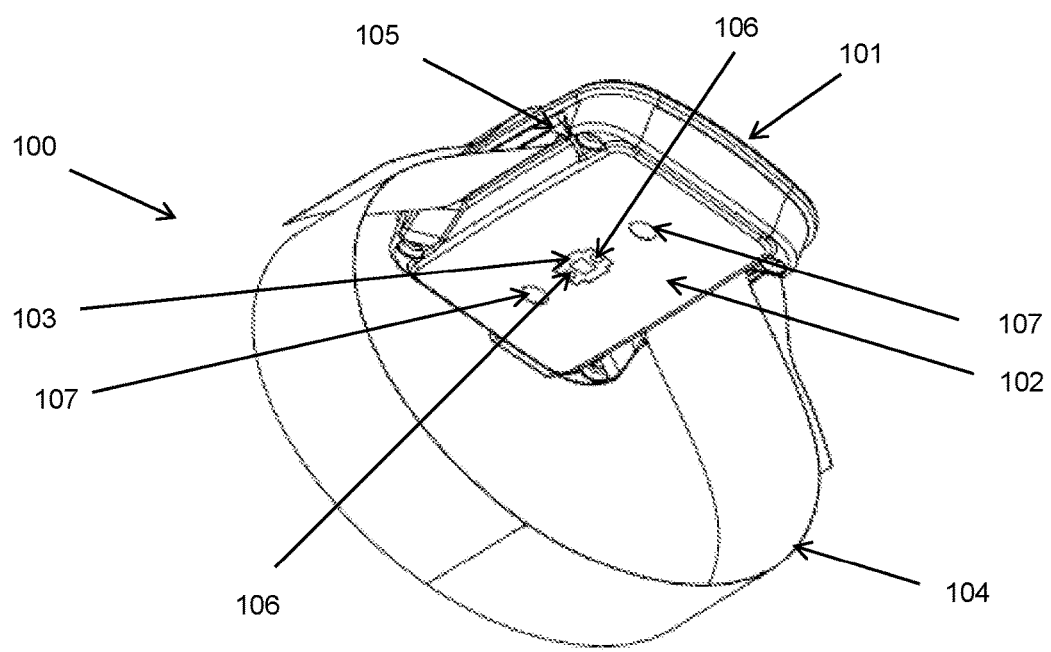
FIG. 1 shows a perspective bottom view of the photoplethysmographic device according to an embodiment of the invention.

FIG. 1 shows a perspective bottom view of the photoplethysmographic device 100 having a housing 101 and a strap or wristband 104. The housing 101 has a contacting surface 102 at the bottom side of the housing 101, which is to be brought into contact with a subject's skin. The contacting surface has a photoplethysmographic (PPG) sensor 103, comprising a photodetector and Light Emitting Diodes 106 (LEDS) positioned laterally of the photodetector. The device 100 can for example be applied to the subject's wrist, however other body parts, i.e limbs and parts thereof may also apply. The strap or wristband 104 can for example be connected to the housing 101 by pulling the strap or wristband end through recesses 105 of the housing. This way a user or wearer can manually tighten the device 100 as much as is required. On the contacting surface 102 one or more pressure sensors 107 can be provided. The pressure sensors 107 can be of the resistive type, such as Flexiforce™ sensors, which are flat and can easily be mounted on the contacting surface 102. Other pressure sensor types may also apply. Within the housing 101 a control unit is accommodated, electrically connected to the PPG sensor 103 and pressure sensors 107.

The control unit may comprise a processor, memory and in- and output circuitry. In the memory a computer program having executable instructions to operate the processor may be stored. The pressure sensors 107 and PPG sensor 103 produce data which may be digitized using AD-converters for processing in the control unit. The computer program allows the control unit read the pressure data from the pressure sensors 107 to determine whether the pressure between the sensors 107 is between a range as described, preferred for performing photoplethysmographic measurements. The control unit determines the heart rhythm based on variations in a PPG signal from the PPG sensor.

Figure 2:
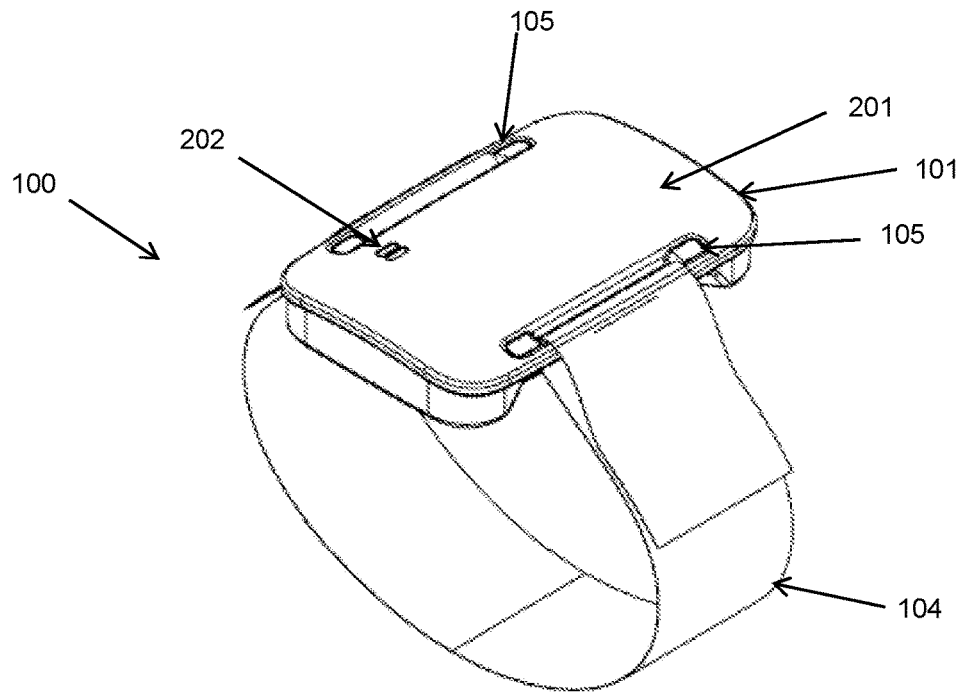
FIG. 2 shows a perspective top view of the photoplethysmographic device according to an embodiment of the invention.

FIG. 2 shows a perspective top view of the photoplethysmographic device 100. In FIG. 2 a cover 201 of the housing 101 is shown. The cover has an opening 202 for a speaker or buzzer as audible alarm for example. Other output indicators may be provided, such as a visual indicator and/or an LCD screen for displaying measurement results. The measurements results can also be transmitted to other equipment such as a PC or smartphone for further processing, preferably wireless using Bluetooth or wireless LAN for example.

Using the pressure sensor data, the control unit can evaluate the photoplethysmographic data from the PPG sensor for judging and weighing to make inferences from these data relating to the heart rhythm to be determined from the photoplethysmographic data. The measured pressure can be used to compensate or calibrate the photoplethysmographic data to make the device 100 more tolerant for motion or other mechanical disturbances.

The signal from the pressure sensors 107 can also be used to determine a reliability factor for the signal from the PPG sensor 103. When for example the measured pressure is outside predetermined upper and lower limits corresponding to a very tight fastening of the wristband and a loose wristband respectively, or when a large variation in the PPG signal i.e. an artefact is detected, the reliability factor is assigned a minimal value, whereas when the measured pressure is within these limits, the reliability factor may be assigned a nominal value for example. When the measured pressure is within a preferred range, the reliability factor may be assigned a high value.

The control unit can save measurements from the PPG signal at predetermined time intervals preceding an actual measurement in a running history. A measurement is saved into the running history when the reliability factor is high enough, i.e. high or nominal in the above describe example. The control unit may indicate a heart rhythm taking into account the actual measurements from the PPG sensor signal and the history of PPG measurements.

The reliability factor can also be used to weigh the actual PPG measurements versus the history of PPG measurements. With a high reliability factor, the control unit may determine a heart rhythm depending more on the actual PPG measurements and less on the history of PPG measurements, and with a low reliability factor, the indicated heart rhythm may be depending more on the history of PPG measurements and less on the actual measurement. Also the history length, i.e. the number of measurements extending from the actual measurement can be varied depending on the reliability factor.

When the pressure determined by the sensors 107 fall within the upper or lower limits, or within the preferred range, the control unit can activate the audible or visual alarm 202. Vice versa, the control unit can also produce an alarm when the measured pressure falls outside the upper or lower limits of preferred range. In a similar way, the control unit can turn the LEDs 106 of the PPG sensor 103 off, when it is detected that the pressure on the pressure sensors 107 is too low so that it can be assumed that the device 100 is not worn by a subject. The LEDs 106 can be turned on when the pressure exceeds a lower limit wherein it can be assumed that the device 100 is being worn by a subject and photoplethysmographic measurements are required. When the measured pressure is too high, above which the PPG sensor can no longer accurately establish a heart rhythm, the LEDs may also be turned off.

Figure 3:
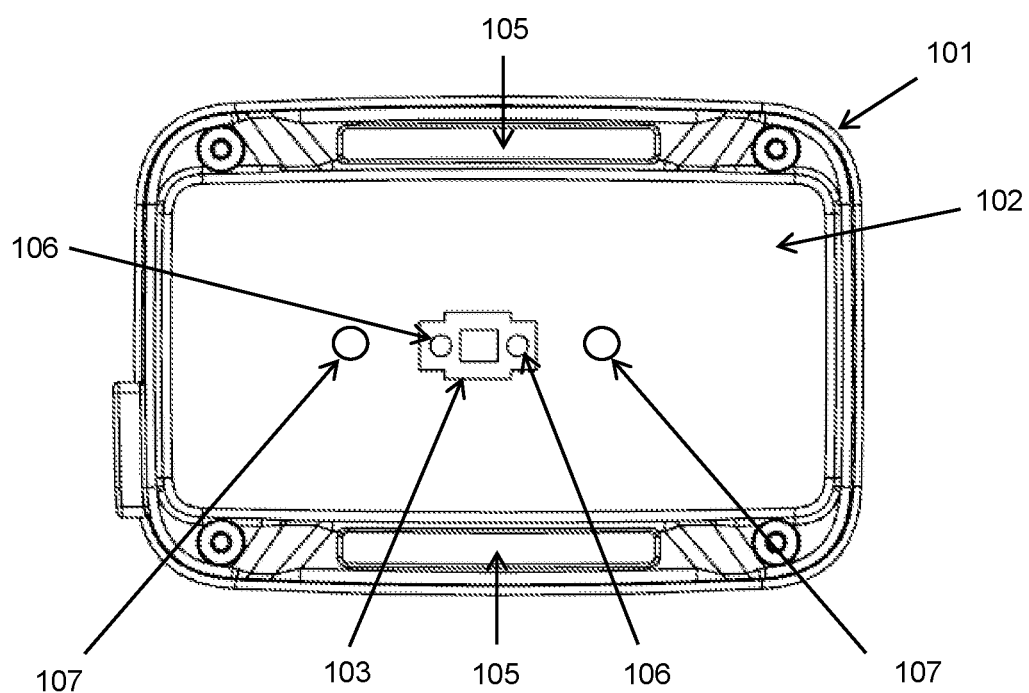
FIG. 3 shows a bottom view of the photoplethysmographic device according to an embodiment of the invention.

FIG. 3 shows a bottom view of the photoplethysmographic device 100 according to an embodiment of the invention. The pressure sensors 107 may be placed laterally to the PPG sensor 103. Two or more pressure sensors 107 may also detect uniform pressure distribution across the contacting surface, i.e. correct placement. Preferably the pressure sensors 107 are placed adjacent to the PPG sensor 103. The PPG sensor 103 has a central position relative to the pressure sensors 107 which consequently surround the PPG sensor 103.

The pressure sensors 107 and PPG sensor 103 are preferably mounted flush with the contacting surface 102. To achieve this, the contacting surface may have a recess for each sensor wherein each sensor is mounted respectively.

REFERENCE NUMERALS 100 photoplethysmographic device
101 housing
102 contacting surface
103 photoplethysmographic (PPG) sensor
104 wristband
105 recess
106 LED
107 pressure sensor
201 cover
202 alarm

What is claimed is:

1. Photoplethysmographic device for measuring a heart rhythm, comprising a housing having a contacting surface and a control unit;
   a photoplethysmographic sensor mechanically mounted to the contacting surface and connected to the control unit, wherein the control unit is arranged to receive a photoplethysmographic signal from the photoplethysmographic sensor, wherein the control unit is arranged for determining a heart rhythm from the photoplethysmographic signal;
   a fastening band having a first end and a second end, the first end and second end attached to the device for attaching the device to a subject with the contacting surface contacting the subject's skin;
   a pressure sensor mounted to the contacting surface in close proximity to the photoplethysmographic sensor;
   wherein the control unit is arranged for determining whether the pressure from the pressure sensor is in a range suitable for photoplethysmographic measurement by the photoplethysmographic sensor, wherein the control unit is arranged for:
   determining a reliability factor for the PPG measurements from the pressure signal; and
   determining a heart rhythm using an actual photoplethysmographic measurement and a running history of measurements of the photoplethysmographic signal; and
   wherein a measurement of the photoplethysmographic signal is saved in the running history when the reliability factor is higher than a threshold.

2. Photoplethysmographic device according to claim 1, wherein the control unit is arranged for comparing a pressure signal strength from the pressure sensor with a first threshold value.

3. Photoplethysmographic device according to claim 1, wherein the control circuit is further arranged for comparing the pressure signal strength from the pressure sensor with a second threshold value, the second threshold value being higher than the first threshold value.

4. Photoplethysmographic device according to claim 3, further comprising an indicator connected to the control unit, wherein the control unit is arranged for activating the indicator when the pressure signal strength from the pressure sensor is equal to or exceeds the first threshold value and the pressure signal strength is equal to or less than the second threshold value.

5. Photoplethysmographic device according to claim 4, wherein the indicator is a sound alarm.

6. Photoplethysmographic device according to claim 1, wherein the photoplethysmographic sensor has a light source, and wherein the control unit is arranged for:
   comparing the pressure signal strength with a third threshold value; and wherein the control unit is arranged for deactivating the light source in the photoplethysmographic sensor when the pressure signal strength from the pressure sensor is equal to or less than the third threshold value.

7. Pressure sensor according to claim 6, wherein the control unit is arranged for deactivating the light source in the photoplethysmographic sensor when the pressure signal strength from the pressure sensor is equal to or greater than the second threshold value.

8. Photoplethysmographic device according to claim 1, wherein at least one of the photoplethysmographic sensor and the pressure sensor are mounted flush with the contacting surface.

9. Photoplethysmographic device according to claim 2, wherein the control circuit is further arranged for comparing the pressure signal strength from the pressure sensor with a second threshold value, the second threshold value being higher than the first threshold value.

10. Photoplethysmographic device according to claim 9, further comprising an indicator connected to the control unit, wherein the control unit is arranged for activating the indicator when the pressure signal strength from the pressure sensor is equal to or exceeds the first threshold value and the pressure signal strength is equal to or less than the second threshold value.

11. Photoplethysmographic device according to claim 5, wherein the indicator is a sound alarm.

* * * * *